United States Patent [19]
Scholl

[11] Patent Number: 6,110,175
[45] Date of Patent: Aug. 29, 2000

[54] SURGICAL CHISEL AND METHOD OF USING SAME

[75] Inventor: Christopher Hargest Scholl, West Chester, Pa.

[73] Assignee: Synthes (USA), Paoli, Pa.

[21] Appl. No.: 09/233,060

[22] Filed: Jan. 20, 1999

[51] Int. Cl.[7] .................................................. A61B 17/32
[52] U.S. Cl. .............................................................. 606/79
[58] Field of Search ................................. 606/11, 54, 84, 606/85, 99, 79, 86

[56] References Cited

U.S. PATENT DOCUMENTS

| | | |
|---|---|---|
| 1,951,278 | 3/1934 | Ericsson . |
| 2,187,852 | 1/1940 | Friddle . |
| 2,222,517 | 11/1940 | Price . |
| 2,239,088 | 4/1941 | Ettinger . |
| 2,327,434 | 8/1943 | Johnston . |
| 2,441,765 | 5/1948 | Hopkins . |
| 2,496,126 | 10/1950 | Haboush . |
| 2,536,964 | 1/1951 | Stephens . |
| 2,716,406 | 8/1955 | Reymann et al. . |
| 2,834,342 | 5/1958 | Yost . |
| 2,874,691 | 2/1959 | Mason . |
| 3,002,514 | 10/1961 | Deyerle . |
| 3,025,853 | 3/1962 | Mason . |
| 3,216,414 | 11/1965 | Street . |
| 3,486,500 | 12/1969 | Ball et al. . |
| 4,239,045 | 12/1980 | Schlein . |
| 4,787,378 | 11/1988 | Sodhi . |
| 4,881,534 | 11/1989 | Uhl et al. . |
| 4,881,537 | 11/1989 | Henning . |
| 4,969,887 | 11/1990 | Sodhi . |
| 4,978,349 | 12/1990 | Frigg . |
| 5,409,489 | 4/1995 | Sioufi . |
| 5,437,675 | 8/1995 | Wilson . |
| 5,499,985 | 3/1996 | Hein et al. ................................ 606/99 |
| 5,601,564 | 2/1997 | Gustilo et al. ............................ 606/99 |
| 5,632,745 | 5/1997 | Schwartz . |
| 5,800,437 | 9/1998 | Gustilo et al. ............................ 606/80 |

FOREIGN PATENT DOCUMENTS

| | | |
|---|---|---|
| 948 690 | 8/1949 | France . |
| 2 676 353 A1 | 11/1992 | France . |
| 2 758 712 | 7/1998 | France . |
| 571255 | 9/1977 | U.S.S.R. . |
| 1326260 A1 | 7/1986 | U.S.S.R. . |
| 1574213 A1 | 6/1990 | U.S.S.R. . |

OTHER PUBLICATIONS

P. 51 of DePuy Mfg. Co. Catalog, believed to be published between 1940 and 1949.

*Primary Examiner*—Michael Buiz
*Assistant Examiner*—William Lewis
*Attorney, Agent, or Firm*—Pennie & Edmonds LLP

[57] ABSTRACT

The present invention relates to a surgical chisel for removing a section of bone. The surgical chisel includes a body having a cannulation which extends from the distal end of the body through at least a portion of the body and is configured and dimensioned to receive a guide wire; and a blade attached to the distal end of the body and having a sharp edge for impacting bone. Introducing the guide wire into the cannulation guides the chisel to the section of bone to be removed. The present invention also relates to a method of removing a section of bone with a chisel. The method includes the steps of inserting a portion of a guide wire into a bone; guiding the chisel blade to the section of bone along the guide wire; and impacting the chisel blade into the bone to remove a section thereof.

17 Claims, 5 Drawing Sheets

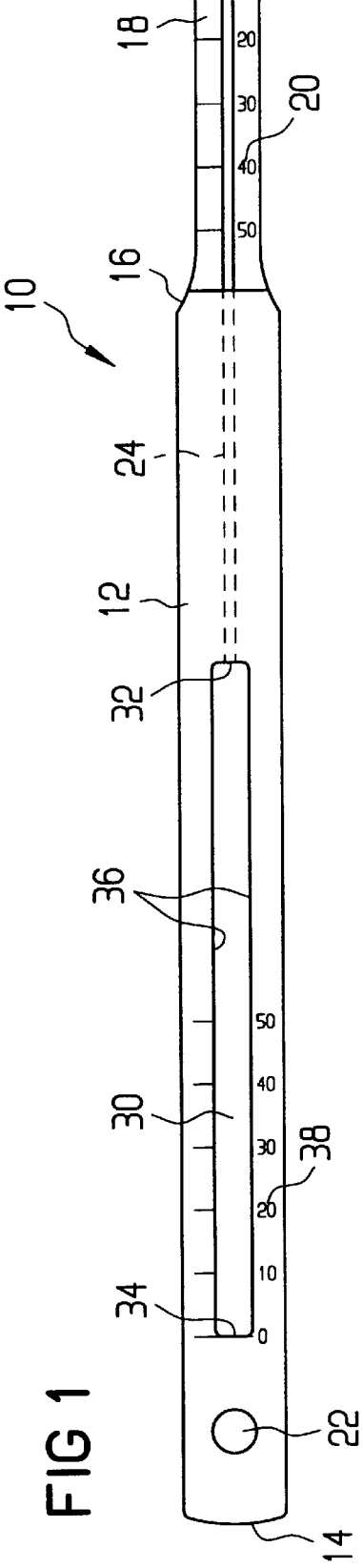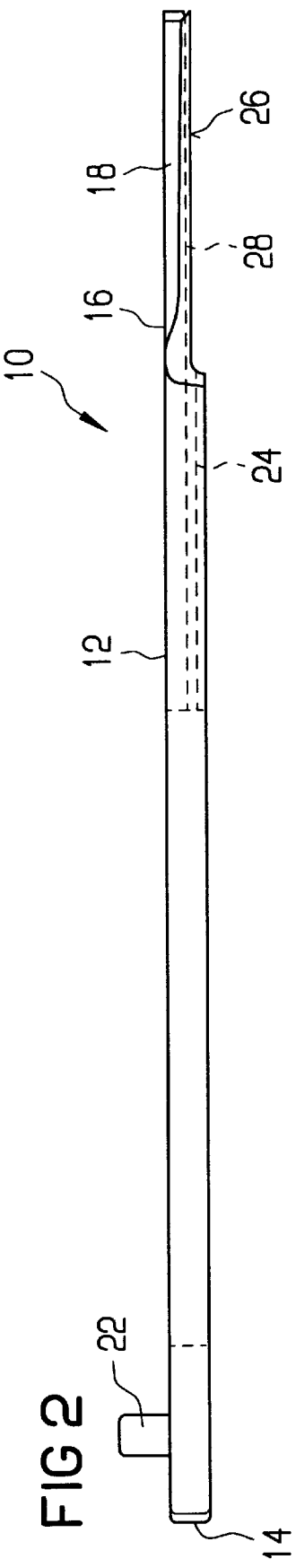

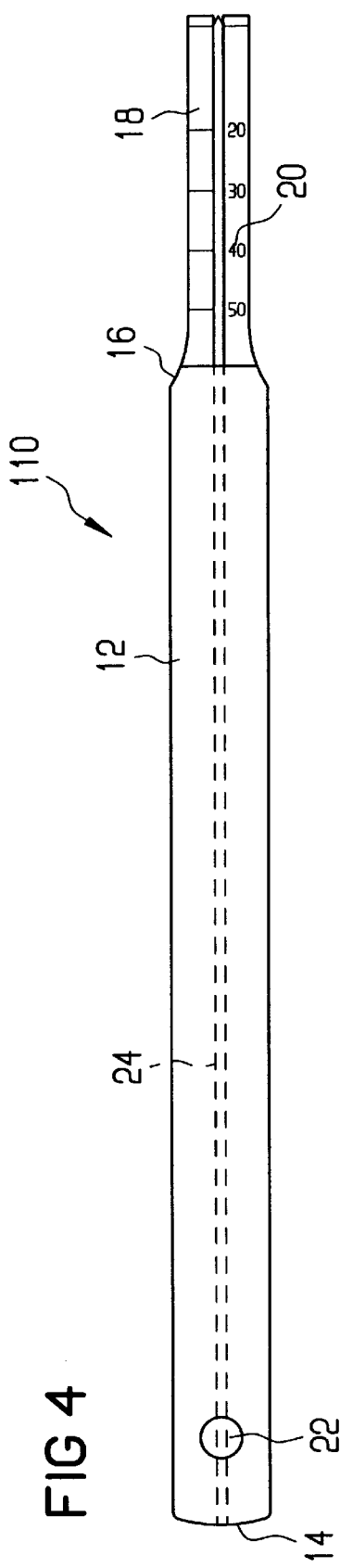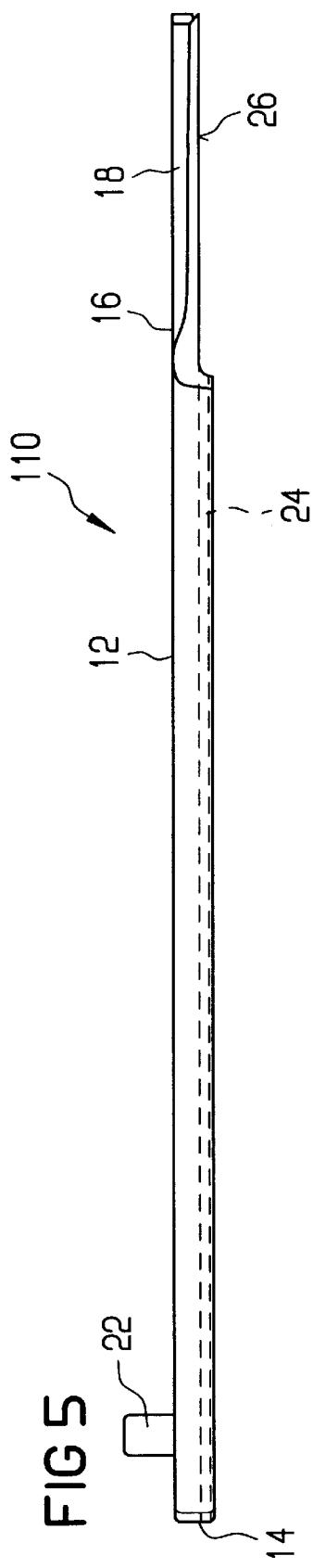

SURGICAL CHISEL AND METHOD OF USING SAME

FIELD OF THE INVENTION

The present invention is directed to a surgical tool, and in particular a surgical chisel and method for removing bone.

BACKGROUND OF THE INVENTION

A guide wire is a flexible wire, usually metallic, used to ensure the proper positioning and placement of a surgical instrument and/or implant. The use of guide wires for orthopaedic applications is well known. For example, cannulated bone screws are widely available. In use, a guide wire is inserted in the desired location, the location of the guide wire is radiographically confirmed, and the guide wire is inserted in the cannulation of the bone screw to guide the bone screw to the implantation site. Cannulated drill bits and hole taps are also available as related instrumentation to facilitate the implantation of the bone screw.

Cannulated blade plates are also widely available. A blade plate, an implant used in various surgical procedures including osteotomies and internal fracture fixation, has a blade extending at an angle from a bone plate. The blade is inserted into the bone while the plate is secured to the bone surface with screws. In some clinical situations, a chisel having a cutting member corresponding in size and shape to the blade is used to create a pathway in the bone for the blade. Although blade plates are available with blades having a wide variety of configurations, the blade (or at least the individual elements that form the blade) are flat elongated members. As a result, it is difficult and costly to manufacture a blade or a chisel with a cannulation. More importantly, forming a cannulation in the blade increases the blade size. The increased size necessitated by the cannulation and the resulting adverse consequences (e.g. stress shielding, excessive removal of bone, etc.) can be particularly problematic in the small sized blade plates which are typically used for infants, children, and adults of modest stature. Unfortunately, chisels are ordinarily used in these patient populations.

In an effort to capitalize on the benefits of guide wires yet eliminate the complications associated with cannulations, alternative implant designs have been developed. U.S. Pat. Nos. 2,222,517 and 2,239,088 and Soviet Union No. 571, 255 disclose a fracture fixation nail having a groove for a guide wire. U.S. Pat. No. 2,496,126 discloses a nail/plate fixation device with webs forming a channel for a guide wire. U.S. Pat. Nos. 3,025,853 and 3,486,500 both disclose an implant that has an aperture for an introducer in which the aperture is located on a bone plate and does not extend through the portion of the implant driven into bone. U.S. Pat. No. 4,978,349 discloses a plate with a guide wire groove.

In spite of these advancements in implant design, very little has been done to improve on chisels that can be used with guide wires. Thus, there exists a need for an improved chisel and method for using a chisel in conjunction with a guide wire.

SUMMARY OF THE INVENTION

The present invention is directed to a surgical chisel for removing a section of bone. The surgical chisel includes a body having a first end, a second end, and a cannulation which extends from the second end through at least a portion of the body and is configured and dimensioned to receive a guide wire; and a blade attached to the second end of the body and having top and bottom surfaces and a sharp edge for impacting bone. Introducing the guide wire into the cannulation guides the chisel to the section of bone to be removed.

In one embodiment, the cannulation extends completely through the body from the second end to the first end. In an alternative embodiment, the body has a rectangular cutout defined by a front edge, a back edge, and two side edges and the cannulation extends from the second end of the body to the front edge of the cutout. In order to assess bone impaction, the body can have markings located along at least one of the cutout side edges. The blade can also have markings for assessing bone impaction.

In a preferred embodiment, the surgical chisel includes a channel extending along the bottom surface of the blade. The channel is contiguous with the cannulation so that a guide wire introduced into the channel slides along the channel and cannulation as the blade impacts the bone.

The body of the surgical chisel may also include a pin located adjacent the first end of the body. The pin is configured and dimensioned to receive a slotted hammer to remove the chisel from the bone.

The blade can have a cross section that is substantially T-shaped. If the surgical chisel is to be used in conjunction with an implant insertable into the bone, the blade cross section substantially conforms in shape and size to that of the implant.

The present invention is also directed to a method of removing a section of bone with a chisel. The method includes the steps of inserting a portion of a guide wire into a bone; guiding the chisel blade to the section of bone along the guide wire; and impacting the chisel blade into the bone to remove a section thereof.

The method can also involve inserting a plate into the void created by the removal of the section of bone and removing the guide wire from the bone. In one embodiment, the step of removing the guide wire from the bone precedes the step of inserting the blade plate into the void. In a preferred embodiment, the chisel body includes a cannulation for receiving and guiding the guide wire to the bone.

BRIEF DESCRIPTION OF THE DRAWINGS

FIG. 1 shows a top view of a first embodiment of the surgical chisel according to the present invention;

FIG. 2 shows a side view of the surgical chisel of FIG. 1;

FIG. 4 shows a top view of a second embodiment of the surgical chisel according to the present invention;

FIG. 5 shows a side view of an alternative embodiment of the surgical chisel according to the present invention;

DESCRIPTION OF THE PREFERRED EMBODIMENTS

Figure 9:
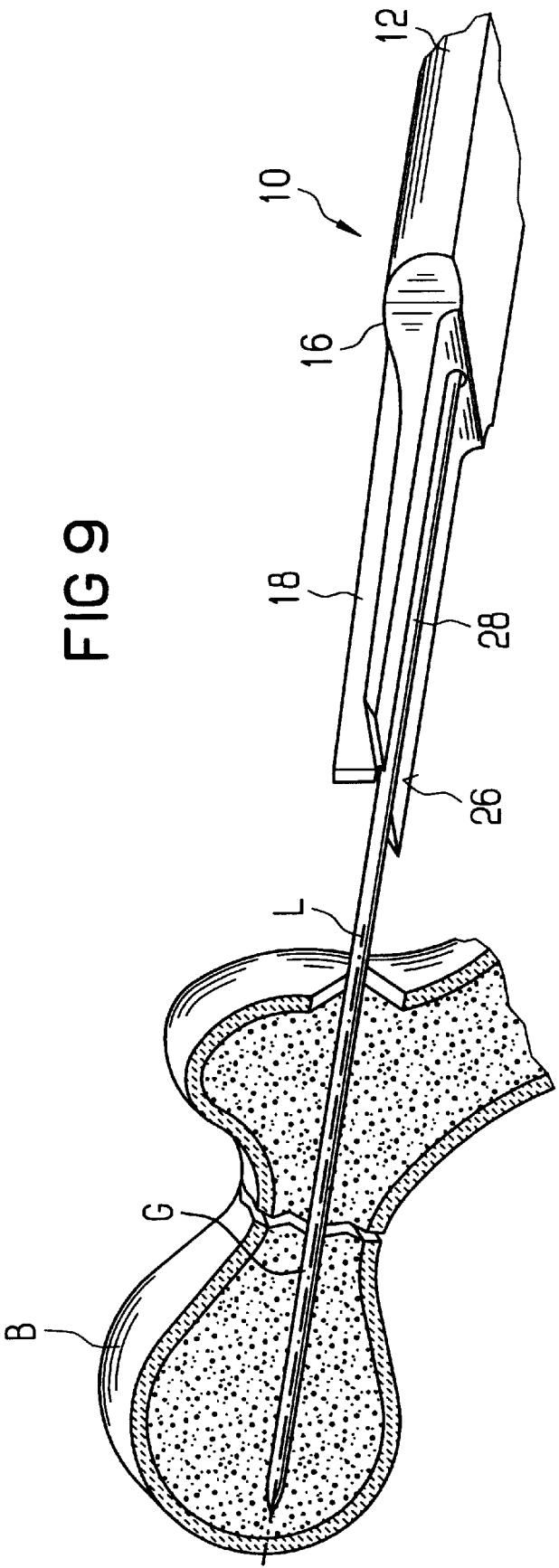
FIG. 9 shows a perspective view of a surgical chisel according to the present invention in use.

FIG. 1 shows a top view of a first embodiment of a surgical chisel 10 according to the present invention. Chisel 10 has a body 12 with proximal 14 and distal 16 ends, and a chisel blade 18 attached to distal end 16 of body 12. In order to facilitate impaction into bone, the tip of chisel blade 18 has at least one sharpened edge. Chisel blade 18 can also have markings 20 for measuring the impaction into bone. A pin 22 is located near proximal end 14 of body 12 for receiving a slap or slotted hammer or other instrument to assist in driving and removal of chisel 10. A cannulation 24 extends from distal end 16 through at least a portion of body 12 so that a guide wire G introduced into cannulation 24 guides chisel 10 to the section of bone B to be removed (FIG. 9). It should be noted that because body 12 has a block-like shape, manufacturing or machining cannulation 24 in body 12 is much simpler and more inexpensive than providing the flat elongated chisel blade 18 with a cannulation.

Figure 3:
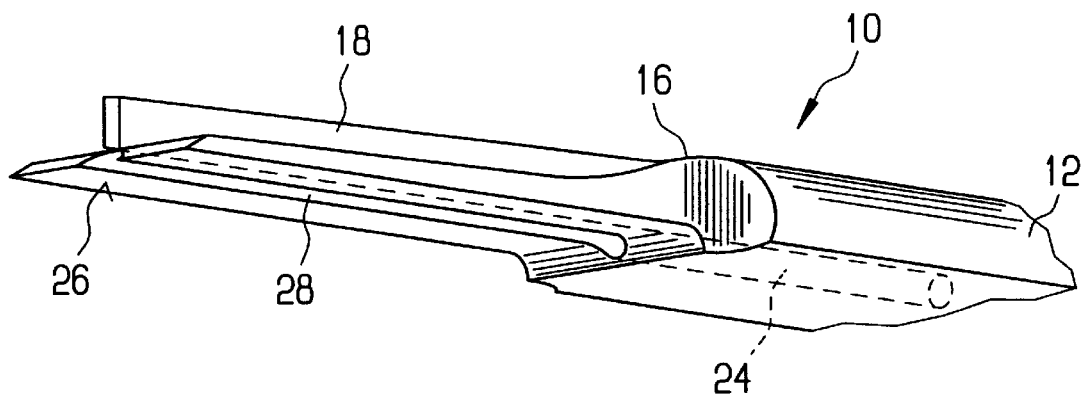
FIG. 3 shows a perspective view of a portion of the surgical chisel of FIG. 1.

As seen best in FIG. 2 and FIG. 3, a bottom surface 26 of chisel blade 18 is provided with a channel 28. Channel 28 is contiguous with cannulation 24 so that guide wire G introduced into channel 28 slides along channel 28 and into cannulation 24 as chisel blade 18 is impacted into bone B (FIG. 9). As long as channel 28 is sized to receive guide wire G, channel 28 can have any suitable cross-section, e.g. semicircular, U-shaped, or V-shaped. Running guide wire G through channel 28 and cannulation 24 helps prevent lateral (left to right) movement of guide wire G. Using channel 28 on chisel blade 18 instead of providing chisel blade 18 with a cannulation has several advantages. First, the difficulties and expense of manufacturing a chisel blade with a cannulation are avoided. It is much cheaper and easier to manufacture a chisel blade with a channel. Additionally, the mechanical strength of a blade with a groove is greater than a blade with a cannulation. Also, the chisel blade does not have to be oversized to accommodate the cannulation. As a result, the blade of the associated blade plate also does not have to be oversized.

Figure 6:
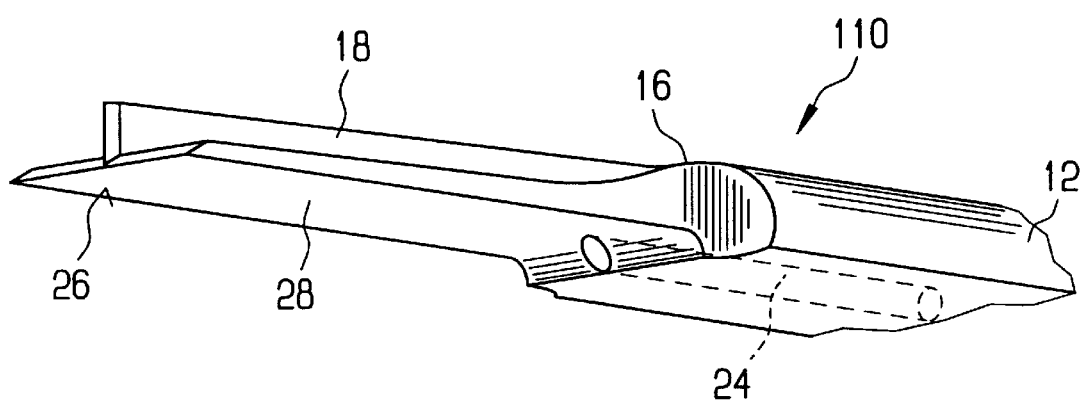
FIG. 6 shows a perspective view of a portion of the surgical chisel of FIG. 5.

FIG. 4 shows a top view of a second embodiment of a surgical chisel 110 according to the present invention. In general, most of the structure of chisel 110 is like or comparable to the structure of chisel 10. Accordingly, the same reference numeral is used for like components and discussion of these components is not believed necessary. Chisel 110 has cannulation 24 for receiving guide wire G to guide chisel 110 to the section of bone B to be removed. Unlike chisel 10, chisel 110 does not have channel 26 on chisel blade 18 (seen best in FIG. 5 and FIG. 6). Experimental studies have indicated that even without a channel on the chisel blade, a guide wire through cannulation 24 of chisel 110 can still effectively direct chisel 110 to the desired location.

FIG. 1 and FIG. 4 illustrate another important difference between chisel 10 and chisel 110. In chisel 110, cannulation 24 extends completely through body 12. In chisel 10, cannulation 24 extends through only a portion of body 12. Body 12 of chisel 10 has a cutout 30 defined by a front edge 32, a back edge 34, and two side edges 36 so that cannulation 24 extends from distal end 16 of body 12 to front edge 32 of cutout 30.

Providing chisel 10 with cutout 30 further simplifies the manufacturing and reduces the production cost of the chisel. Furthermore, as the free end of the guide wire can be visualized, cutout 30 provides an additional means for determining the depth of impaction of chisel blade 18 into bone. In this regard, body 12 has indicia 38 located near side edges 36 of cutout 30 for assessing impaction into bone. It should be noted that chisel 110 can be provided with a cutout identical to cutout 30. Stated differently, the use of a cutout does not depend on the presence or absence of a channel on the blade.

Figure 7:
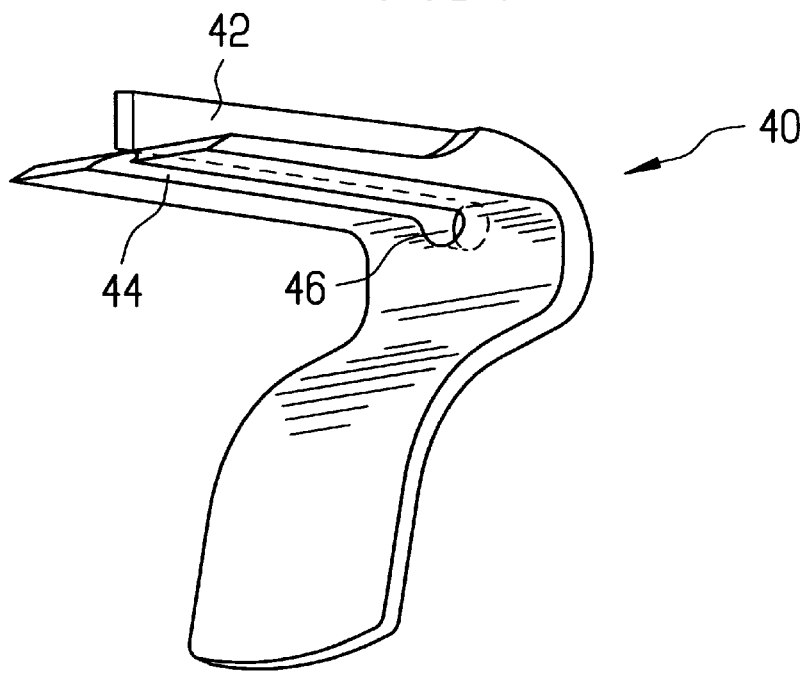
FIG. 7 shows an osteotomy plate that can be used with the surgical chisel according to the present invention.
Figure 8:
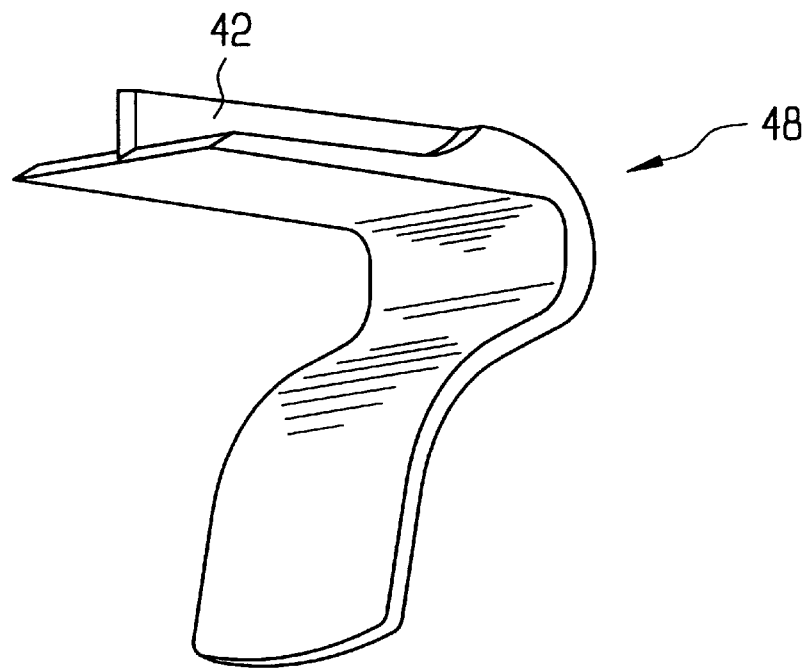
FIG. 8 shows another osteotomy plate that can be used with the surgical chisel according to the present invention.

Chisel 10, 110 can be used in various clinical applications, including those in which bone is being removed without the subsequent implantation of an implant such as a blade plate. In situations in which chisel 10, 110 is to be used in conjunction with a blade plate, the cross section of chisel blade 18 substantially conforms in shape and size to the cross section of the blade of the blade plate. For example, FIG. 7 shows a blade plate 40 having a blade 42 that has a T-shaped cross section. As seen best in FIG. 3 and FIG. 6, the cross sections of chisel 10, 110 are T-shaped and substantially conform to the cross section of blade 42. Blade 42 has a groove 44 and an aperture 46 for a guide wire. As it is expected that after chisel 10, 100 has removed the desired amount of bone there will be a tight press fit between the blade of the blade plate and the remaining bone, the blade plate can only be implanted at the desired location and in the desired orientation. Therefore, chisel 10, 110 can be used with an appropriately sized and shaped conventional blade plate that does not have either a cannulation, channel, groove, or any other feature for accommodating a guide wire (as long as the guide wire is removed from the bone before the blade plate is implanted). FIG. 8 shows such a blade plate 48.

The present invention also relates to a method of using chisel 10, 110 and such a method is now described referring primarily to FIG. 9. In use, the surgeon inserts guide wire G under fluoroscopy or other image intensification to monitor the positioning of the guide wire. Once satisfied with the location of guide wire G, the surgeon runs the free end of guide wire G through cannulation 24 so that chisel 10, 110 will be properly positioned. A chisel guide (not shown) can be placed on the exterior of chisel 10, 110 so that the surgeon can align the chisel blade 18 with the longitudinal axis L of bone B. Using a hammer or other driving instrument, the surgeon then impacts chisel blade 18 into bone B. In this regard, markings 20 and/or indicia 38 can be used to determine the depth of penetration of chisel blade 18. After the desired depth of penetration has been achieved, the chisel blade is removed from bone B. As previously noted, pin 22 can be used to facilitate removal of chisel blade. If a blade plate such as blade plate 40 (i.e. having some structural feature to accommodate guide wire G) is to be used, then the surgeon runs the free end of guide wire G through aperture 46. Alternatively, guide wire G can be removed before the blade plate is implanted.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A surgical chisel for removing a section of bone comprising:
    a body having a first end, a second end, and a cannulation which extends from the second end through at least a portion of the body and is configured and dimensioned to receive a guide wire; and
    a blade attached to the second end of the body and having top and bottom surfaces and a sharp edge for impacting bone,
    wherein introduction of a guide wire into the cannulation guides the chisel to the section of bone to be removed and the blade has a cross section that is substantially T-shaped.

2. The surgical chisel of claim 1 further comprising a channel extending along the bottom surface of the blade and being contiguous with the cannulation so that a guide wire introduced into the channel slides along the channel and cannulation as the blade impacts the bone.

3. The surgical chisel of claim 1 wherein the body includes a pin located adjacent the first end of the body, the pin being configured and dimensioned to receive a slotted hammer to remove the chisel from the bone.

4. The surgical chisel of claim 1 wherein the blade has markings for assessing bone impaction.

5. A method of removing a section of bone with with the surgical chisel of claim 1, the method comprising the steps of:

inserting a portion of a guide wire into a bone, the guide wire having a proximal end and a distal end, the proximal end being inserted into the bone;

guiding the chisel blade to the section of bone along the guide wire; and impacting the chisel blade into the bone to remove a section thereof.

6. The method of claim 5 further comprising the steps of:

inserting a plate into the void created by removing the section of bone; and removing the guide wire from the bone.

7. The method of claim 6 wherein the step of removing the guide wire from the bone precedes the step of inserting the blade plate into the void.

8. A surgical chisel for removing a section of bone comprising:

a body having a first end, a second end, and a cannulation which extends from the second end through at least a portion of the body and is configured and dimensioned to receive a guide wire; and a blade attached to the second end of the body and having top and bottom surfaces and a sharp edge for impacting bone, wherein introduction of a guide wire into the cannulation guides the chisel to the section of bone to be removed and the cannulation extends completely through the body from the second end to the first end.

9. A surgical chisel for removing a section of bone comprising:

a body having a first end, a second end, and a cannulation which extends from the second end through at least a portion of the body and is configured and dimensioned to receive a guide wire; and a blade attached to the second end of the body and having top and bottom surfaces and a sharp edge for impacting bone, wherein introduction of a guide wire into the cannulation guides the chisel to the section of bone to be removed and the body has a rectangular cutout defined by a front edge, a back edge, and two side edges, the cannulation extending from the second end of the body to the front edge of the cutout.

10. The surgical chisel of claim 9 wherein the body has markings located along at least one of the cutout side edges for assessing bone impaction.

11. A surgical chisel for preparing a bone to receive an implant insertable into the bone the chisel comprising:

a body having a first end, a second end, and a cannulation which extends from the second end through at least a portion of the body and is configured and dimensioned to receive a guide wire; and a blade attached to the second end of the body and having top and bottom surfaces, a sharp edge for impaction into the bone and a cross section substantially conforming in shape and size to that of the implant;

wherein introduction of a guide wire into the cannulation guides the chisel as the blade impacts the bone and the blade cross section is substantially T-shaped.

12. A surgical chisel for preparing a bone to receive an implant insertable into the bone, the chisel comprising:

a body having a first end, a second end, and a cannulation which extends from the second end through at least a portion of the body and is configured and dimensioned to receive a guide wire; and a blade attached to the second end of the body and having top and bottom surfaces a sharp edge for impaction into the bone and a cross section substantially conforming in shape and size to that of the implant;

wherein introduction of a guide wire into the cannulation guides the chisel as the blade impacts the bone and the cannulation extends completely through the body from the second end to the first end.

13. A surgical chisel for preparing a bone to receive an implant insertable into the bone the chisel comprising:

a body having a first end, a second end, and a cannulation which extends from the second end through at least a portion of the body and is configured and dimensioned to receive a guide wire; and a blade attached to the second end of the body and having top and bottom surfaces a sharp edge for impaction into the bone and a cross section substantially conforming in shape and size to that of the implant;

wherein introduction of a guide wire into the cannulation guides the chisel as the blade impacts the bone and the body has a rectangular cutout defined by a front edge, a back edge, and two side edges, the cannulation extending from the second end of the body to the front edge of the cutout.

14. The surgical chisel of claim 13 further comprising a channel extending along the bottom surface of the blade and being contiguous with the cannulation so that a guide wire introduced into the channel slides along the channel and cannulation as the blade impacts the bone.

15. The surgical chisel of claim 13 wherein the body includes a pin located adjacent the first end of the body, the pin being configured and dimensioned to receive a slotted hammer to remove the chisel from the bone.

16. The surgical chisel of claim 13 wherein the blade has markings for assessing bone impaction.

17. The surgical chisel of claim 13 wherein the body has markings located along at least one of the cutout side edges for assessing bone impaction.

* * * * *